(12) United States Patent
Hung et al.

(10) Patent No.: US 10,216,978 B2
(45) Date of Patent: Feb. 26, 2019

(54) FINGERPRINT IDENTIFICATION DEVICE AND FINGERPRINT IDENTIFICATION METHOD

(71) Applicant: Gingy Technology Inc., Hsinchu (TW)

(72) Inventors: Chun-Lang Hung, Hsinchu (TW); Jen-Chieh Wu, Hsinchu (TW)

(73) Assignee: Gingy Technology Inc., Hsinchu (TW)

( * ) Notice: Subject to any disclaimer, the term of this patent is extended or adjusted under 35 U.S.C. 154(b) by 0 days.

(21) Appl. No.: 15/942,441

(22) Filed: Mar. 31, 2018

(65) Prior Publication Data

US 2018/0225502 A1  Aug. 9, 2018

Related U.S. Application Data

(63) Continuation-in-part of application No. 15/208,619, filed on Jul. 13, 2016, now Pat. No. 9,977,947, which (Continued)

(30) Foreign Application Priority Data

Aug. 26, 2014  (TW) .............................. 103129359 A
Dec. 22, 2014  (TW) .............................. 103144744 A
(Continued)

(51) Int. Cl.
*G06K 9/00* (2006.01)
*G06K 9/20* (2006.01)
(Continued)

(52) U.S. Cl.
CPC ........ *G06K 9/0012* (2013.01); *A61B 5/02416* (2013.01); *A61B 5/1172* (2013.01);
(Continued)

(58) Field of Classification Search
None
See application file for complete search history.

(56) References Cited

U.S. PATENT DOCUMENTS 9,119,539 B1 * 9/2015 Dotan ................ A61B 5/02438
9,218,522 B2  12/2015 Hung
(Continued)

FOREIGN PATENT DOCUMENTS

CN  106326836  1/2017
TW  201101196  1/2011
(Continued)

*Primary Examiner* — Manav Seth
*Assistant Examiner* — David Perlman
(74) *Attorney, Agent, or Firm* — JCIPRNET (57) ABSTRACT

A fingerprint identification device including a light source, a processor, and a light receiver is provided. The light source emits a light beam to an object. The light receiver captures an object image of the object in a time interval. The processor analyzes the object image to obtain a fingerprint image, and performs a fingerprint identification operation on the fingerprint image to obtain a fingerprint identification result. The processor further analyzes the object image to obtain pixel change data of the object image in the time interval, and determines whether the fingerprint image is verified according to the fingerprint identification result and the pixel change data. A fingerprint identification method is also provided.

12 Claims, 4 Drawing Sheets

Related U.S. Application Data is a continuation-in-part of application No. 14/978,237, filed on Dec. 22, 2015, now Pat. No. 9,770,199, and a continuation-in-part of application No. 14/835,130, filed on Aug. 25, 2015, now abandoned.

(60) Provisional application No. 62/533,632, filed on Jul. 17, 2017, provisional application No. 62/486,954, filed on Apr. 18, 2017.

(30) Foreign Application Priority Data

| Nov. 21, 2017 | (CN) | 2017 1 1167931 |
| Dec. 6, 2017 | (CN) | 2017 1 1273483 |

(51) Int. Cl.
*A61B 5/024* (2006.01)
*A61B 5/1172* (2016.01)

(52) U.S. Cl.
CPC ..... *G06K 9/00033* (2013.01); *G06K 9/00087* (2013.01); *G06K 9/2018* (2013.01); *G06K 2009/00939* (2013.01)

(56) References Cited

U.S. PATENT DOCUMENTS

| 9,607,138 B1* | 3/2017 | Baldwin | G06F 21/32 |
| 2007/0189586 A1 | 8/2007 | Monden | |
| 2008/0095412 A1 | 4/2008 | Fujieda et al. | |
| 2011/0150303 A1 | 6/2011 | Dinerstein et al. | |
| 2011/0170750 A1* | 7/2011 | Kropp | A61B 5/02444 |
| | | | 382/124 |
| 2013/0194236 A1 | 8/2013 | Gu et al. | |
| 2014/0051955 A1 | 2/2014 | Tiao et al. | |
| 2014/0294262 A1 | 10/2014 | Schuckers et al. | |
| 2015/0062319 A1 | 3/2015 | Higuchi | |
| 2015/0095816 A1 | 4/2015 | Pan | |
| 2017/0124370 A1* | 5/2017 | He | G06K 9/0012 |

FOREIGN PATENT DOCUMENTS

| TW | I485629 | 5/2015 |
| TW | 201705031 | 2/2017 |

* cited by examiner

FINGERPRINT IDENTIFICATION DEVICE AND FINGERPRINT IDENTIFICATION METHOD

CROSS-REFERENCE TO RELATED APPLICATION

This application is a continuation-in-part application of and claims the priority benefit of U.S. application Ser. No. 15/208,619, filed on Jul. 13, 2016, now pending. The prior U.S. application Ser. No. 15/208,619 is a continuation-in-part application of and claims the priority benefit of U.S. application Ser. No. 14/835,130, filed on Aug. 25, 2015, now pending, which claims the priority benefit of Taiwan application serial no. 103129359, filed on Aug. 26, 2014. The prior U.S. application Ser. No. 15/208,619 is also a continuation-in-part application of and claims the priority benefit of U.S. application Ser. No. 14/978,237, filed on Dec. 22, 2015, now patented, which claims the priority benefit of Taiwan application serial no. 103144744, filed on Dec. 22, 2014. This application also claims the priority benefits of U.S. provisional application Ser. No. 62/486,954, filed on Apr. 18, 2017, U.S. provisional application Ser. No. 62/533,632, filed on Jul. 17, 2017, China application serial no. 201711167931.0, filed on Nov. 21, 2017, and China application serial no. 201711273483.2, filed on Dec. 6, 2017. The entirety of each of the above patent applications is hereby incorporated by reference herein and made a part of this specification.

BACKGROUND OF THE INVENTION

Field of the Invention

The invention relates to an identification technique, and more particularly relates to a fingerprint identification device and a fingerprint identification method.

Description of Related Art

There are various types of biometrics, including face, voice, iris, retina, vein, fingerprint identification, and so on. Since every person has unique fingerprints, which do not easily change with age or physical health, fingerprint identification devices have now become the most commonly used biometric system. Depending on how the sensing is performed, fingerprint identification devices can be divided into optical type, capacitive type, ultrasonic type, thermal induction type, and so on.

However, the traditional fingerprint identification devices are unable to accurately distinguish real fingers from fake ones (living or non-living). Some people may take advantage of this and use silicone material to make fake fingers, which may even have fake fingerprints and sweat pores thereon. When such fake fingers that have silicone properties and fingerprints and sweat pores thereon are pressed against the fingerprint identification device, the fake fingers can also be deformed and have the characteristics of fingerprints and sweat pores and thus may successfully cheat the fingerprint identification device, causing that the fingerprint identification device cannot accurately determine whether it is pressed by the finger of a living body and raising concerns over security breach. Exemplary embodiments of the invention are provided hereinafter.

SUMMARY OF THE INVENTION

The invention provides a fingerprint identification device and a fingerprint identification method, providing a favorable fingerprint identification function to prevent a fake finger from being verified.

A fingerprint identification device according to an embodiment of the invention includes a light source, a processor, and a light receiver. The light source is configured to emit a light beam to an object. The light receiver is coupled to the processor. The light receiver is configured to capture an object image of the object in a time interval. The processor analyzes the object image to obtain a fingerprint image, and the processor performs a fingerprint identification operation on the fingerprint image to obtain a fingerprint identification result. The processor further analyzes the object image to obtain pixel change data of the object image in the time interval, and the processor determines whether the fingerprint image is verified according to the fingerprint identification result and the pixel change data.

In an embodiment of the invention, the fingerprint identification device further includes a touch sensor. The touch sensor is coupled to the processor. The touch sensor is configured to sense whether the object is placed on the touch sensor to output a sensing signal to the processor. The processor determines whether to drive the light source to enable the light source to emit the light beam according to the sensing signal.

In an embodiment of the invention, the light beam emitted by the light source is a single-wavelength light beam or a multi-wavelength light beam.

In an embodiment of the invention, the object image captured by the light receiver includes a plurality of object pictures. The processor selects one of the object pictures for analysis to obtain the fingerprint image.

In an embodiment of the invention, the object image captured by the light receiver includes a plurality of object pictures. The processor analyzes at least one partial block of each of the object pictures respectively to obtain pixel data corresponding to the object pictures in the time interval. The processor collects statistics of the pixel data to obtain the pixel change data.

In an embodiment of the invention, the pixel data is a total red pixel value of the at least one partial block of each of the object pictures respectively.

In an embodiment of the invention, the pixel data is an operation result of red pixel data, green pixel data, and blue pixel data of the at least one partial block of each of the object pictures respectively.

In an embodiment of the invention, the processor analyzes the pixel change data to determine whether a pixel value in the pixel change data presents a periodical change in the time interval.

In an embodiment of the invention, when the processor determines that the pixel value in the pixel change data presents the periodical change in the time interval, the processor further generates heartbeat information according to a periodical change result of the pixel value in the time interval.

A fingerprint identification method according to an embodiment of the invention is adapted for a fingerprint identification device. The fingerprint identification method includes: emitting a light beam to an object by a light source; capturing an object image of the object in a time interval by a light receiver; analyzing the object image to obtain a fingerprint image, and performing a fingerprint identification operation on the fingerprint image to obtain a fingerprint identification result; further analyzing the object image to obtain pixel change data of the object image in the time interval; and determining whether the fingerprint image is verified according to the fingerprint identification result and the pixel change data.

In an embodiment of the invention, the fingerprint identification method further includes: sensing whether the object is placed on a touch sensor to output a sensing signal by the touch sensor; and determining whether to drive the light source to enable the light source to emit the light beam according to the sensing signal.

In an embodiment of the invention, the light beam emitted by the light source is a single-wavelength light beam or a multi-wavelength light beam.

In an embodiment of the invention, the object image captured by the light receiver includes a plurality of object pictures, and analyzing the object image to obtain the fingerprint image includes: selecting one of the object pictures for analysis to obtain the fingerprint image.

In an embodiment of the invention, the object image captured by the light receiver includes a plurality of object pictures, and further analyzing the object image to obtain the pixel change data of the object image in the time interval includes: analyzing at least one partial block of each of the object pictures respectively to obtain pixel data corresponding to the object pictures in the time interval; and collecting statistics of the pixel data to obtain the pixel change data.

In an embodiment of the invention, the pixel data is a total red pixel value of the at least one partial block of each of the object pictures respectively.

In an embodiment of the invention, the pixel data is an operation result of red pixel data, green pixel data, and blue pixel data of the at least one partial block of each of the object pictures respectively.

In an embodiment of the invention, determining whether the fingerprint image is verified according to the fingerprint identification result and the pixel change data includes: analyzing the pixel change data to determine whether a pixel value in the pixel change data presents a periodical change in the time interval.

In an embodiment of the invention, the fingerprint identification method further includes: further generating heartbeat information according to a periodical change result of the pixel value in the time interval when the pixel value in the pixel change data presents the periodical change in the time interval.

Based on the above, in the fingerprint identification device and the fingerprint identification method according to one or some embodiments of the invention, whether the object to be identified is a real finger is determined according to the pixel change data of the object image of the object in a time interval, and the fingerprint identification operation is further performed, so as to prevent a fake finger from being verified.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

In order to make the invention more comprehensible, exemplary embodiments of the invention are described in detail hereinafter, but it should be noted that the invention should not be construed as being limited to these embodiments. Some embodiments may be combined where appropriate. Moreover, elements/components/steps with the same reference numerals represent the same or similar parts in the drawings and embodiments.

Figure 1:
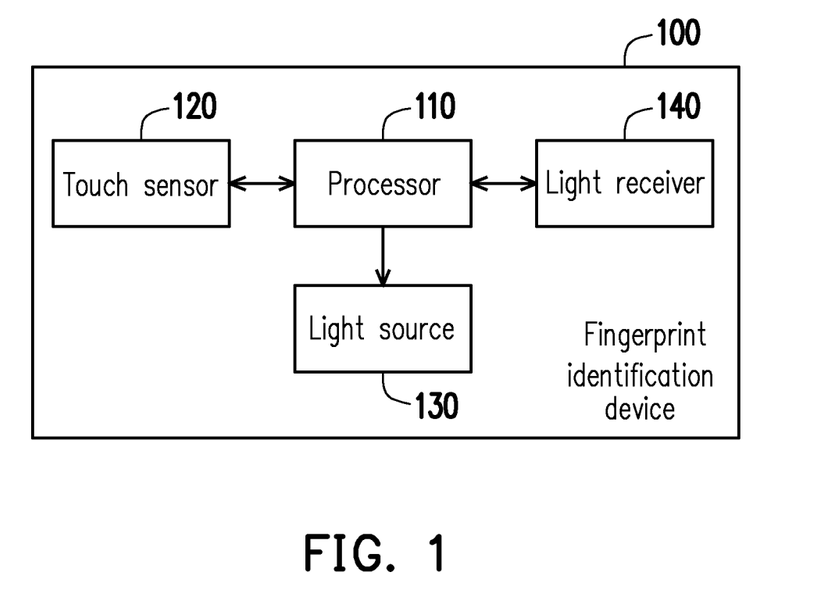
FIG. 1 is a block diagram of the fingerprint identification device according to an embodiment of the invention.

FIG. 1 is a block diagram of a fingerprint identification device according to an embodiment of the invention. Referring to FIG. 1, in this embodiment, a fingerprint identification device 100 includes a processor 110, a touch sensor 120, a light source 130, and a light receiver 140. The processor 110 is coupled to the touch sensor 120, the light source 130, and the light receiver 140. In this embodiment, the processor 110 senses whether an object is placed on the fingerprint identification device 100 via the touch sensor 120. When the touch sensor 120 senses the object, the touch sensor 120 outputs a sensing signal to the processor 110, such that the processor 110 drives the light source 130.

In this embodiment, the light source 130 is configured to emit a light beam to the object, such that the light beam is reflected by a surface of the object to the light receiver 140. The light receiver 140 is configured to capture an object image of the object in a time interval, and outputs the object image to the processor 110. In this embodiment, the processor 110 analyzes the object image to obtain an object picture and performs a fingerprint identification operation on a fingerprint in the object picture to obtain a fingerprint identification result. The processor 110 further analyzes the object image to obtain pixel change data of the object image in the time interval. In this embodiment, the fingerprint identification device 100 combines the fingerprint identification result and a result of analyzing the pixel change data to determine whether a fingerprint image provided by the object is verified.

In other words, in addition to identifying a fingerprint characteristic, the fingerprint identification device 100 of this embodiment further analyzes the pixel change data of the object in the time interval to determine whether the object is a real finger. For example, if the fingerprint characteristic in the fingerprint image matches registered fingerprint characteristic data that is stored in the fingerprint identification device 100 in advance, but the pixel change data of the object in the time interval does not match a preset condition, the fingerprint identification device 100 determines that the object is not a real finger, and the fingerprint image of the object cannot be verified. In addition, for example, if the fingerprint characteristic in the fingerprint image matches the registered fingerprint characteristic data that is stored in the fingerprint identification device 100 in advance, and the pixel change data of the object in the time interval matches the preset condition, the fingerprint identification device 100 determines that the object is a real finger, and determines that the fingerprint image of the object is verified. In other words, the fingerprint identification device 100 of this embodiment may prevent the fingerprint characteristic provided by a fake finger from being verified according to the two conditions described above.

Those skilled in the art may understand the identification and analysis of the fingerprint characteristic described in the embodiment from the teaching, suggestion, and description of implementation of the common knowledge in this field and thus details thereof are not repeated hereinafter.

In this embodiment, the processor 110 may be a central processing unit (CPU), a System on Chip (SOC) or other programmable microprocessors for general use or special use, a digital signal processor (DSP), a programmable controller, an application specific integrated circuit (ASIC), a programmable logic device (PLD), other similar processing devices, or a combination of these devices, for example. The fingerprint identification device 100 further includes a storage device, wherein the storage device may be a fixed or portable random access memory (RAM) in any form, a read-only memory (ROM), a flash memory, similar devices, or a combination of the foregoing devices, for example. In this embodiment, the storage device is configured to store the object image data, object picture data, a plurality of modules, and so on of each embodiment of the invention, such that the processor 110 may access the storage device and execute the data and modules to implement a fingerprint identification method described in the embodiments of the invention.

In this embodiment, the light source 130 is configured to emit a single-wavelength light beam or a multi-wavelength light beam, which has a wavelength of 400 nm to 3000 nm. In other words, when the touch sensor 120 senses the object, the processor 110 may drive the light source 130 to enable the light source 130 to emit the single-wavelength light beam or the multi-wavelength light beam to the object.

In this embodiment, the light receiver 140 is a charge coupled device (CCD) or a complementary metal-oxide semiconductor (CMOS), for example. Specifically, in this embodiment, the light receiver 140 may continuously receive a light beam reflected by the object in a time interval, so as to capture a single-color or multi-color object image, and the light receiver 140 outputs data of the object image to the processor 110 for the processor 110 to perform analysis according to the data of the object image. In this embodiment, the light receiver outputs the object image in a YUV format, a RGB format, or a RAW RGB format to the processor 110, for example.

In this embodiment, the touch sensor 120 is a capacitive sensor, for example, and the sensing signal is a capacitive signal. The touch sensor 120 may be disposed in a metal frame on a pressing plate having a fingerprint sensing region or be incorporated into the pressing plate, for example. The invention is not intended to limit the touch sensor 120 to a certain form. In other words, when the object is placed on the fingerprint sensing region of the fingerprint identification device 100, if the object is a real finger, the touch sensor 120 senses a capacitance change and therefore outputs the capacitive signal to the processor 110 according to the capacitance change, such that the processor 110 drives the light source 130. On the other hand, if the object is a fake finger, the touch sensor 120 does not sense a capacitance change and therefore does not output the capacitive signal to the processor 110, such that the processor 110 does not drive the light source 130. However, in an embodiment, the fingerprint identification device 100 may not include the touch sensor 120, and the light source 130 may be turned on constantly or the processor 110 may determine whether to drive the light source 130 by other methods. Nevertheless, the invention is not limited thereto.

Exemplary embodiments of various device configurations of the fingerprint identification device of the invention are described hereinafter with reference to the embodiments of FIG. 2A to FIG. 2C. Nevertheless, the invention is not limited thereto.

Figure 2A:
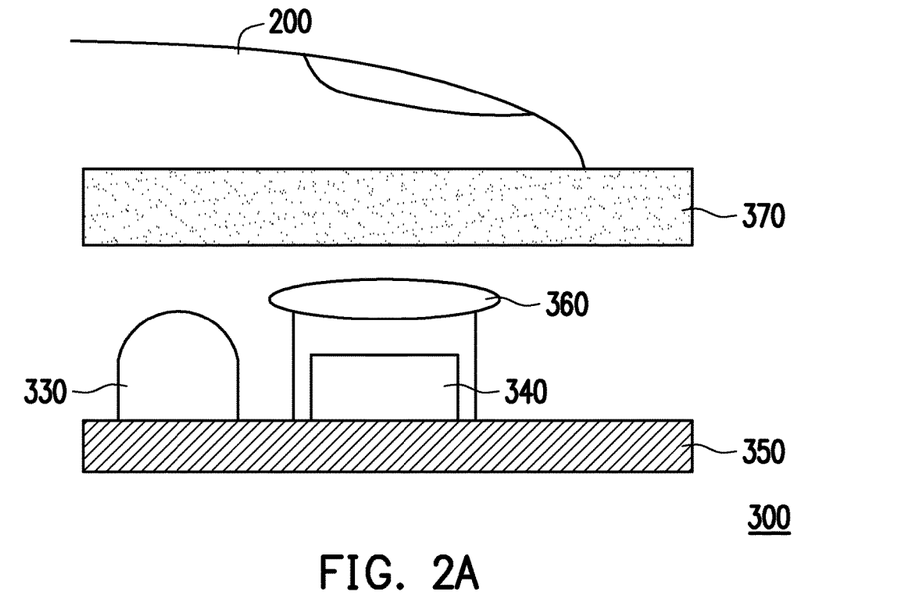
FIG. 2A is a schematic diagram of the fingerprint identification device according to an embodiment of the invention.

FIG. 2A is a schematic diagram of the fingerprint identification device according to an embodiment of the invention. Referring to FIG. 2A, in this embodiment, a fingerprint identification device 300 includes a light source 330, a light receiver 340, a substrate 350, a lens 360, and a pressing plate 370. The light source 330 and the light receiver 340 are disposed on the substrate 350, and the light receiver 340 includes the lens 360. In this embodiment, when an object 200 is placed on a fingerprint sensing region of the pressing plate 370, the light source 330 is driven to emit a light beam to the object 200. The light receiver 340 obtains an image of the object 200 on the pressing plate 370 via the lens 360, so as to output an object image to a processor of the fingerprint identification device.

Figure 2B:
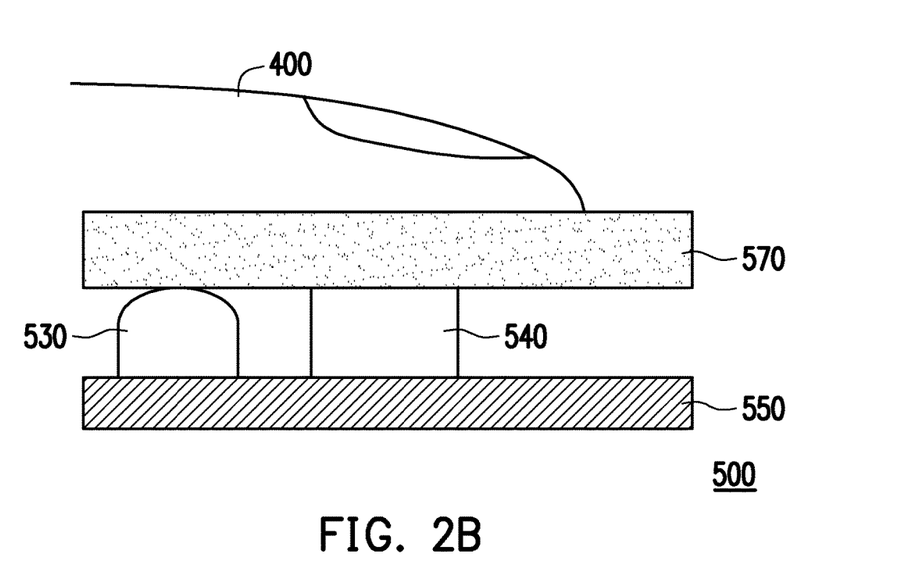
FIG. 2B is a schematic diagram of the fingerprint identification device according to another embodiment of the invention.

FIG. 2B is a schematic diagram of the fingerprint identification device according to another embodiment of the invention. Referring to FIG. 2B, in this embodiment, a fingerprint identification device 500 includes a light source 530, a light receiver 540, a substrate 550, and a pressing plate 570. The light source 530 and the light receiver 540 are disposed on the substrate 550. In this embodiment, when an object 400 is placed on a fingerprint sensing region of the pressing plate 570, the light source 530 is driven to emit a light beam to the object 400. The light receiver 540 captures an image of the object 400 on the pressing plate 570, so as to output an object image to a processor of the fingerprint identification device. In this embodiment, the light receiver 540 may also directly capture the object image formed on the pressing plate 570.

Figure 2C:
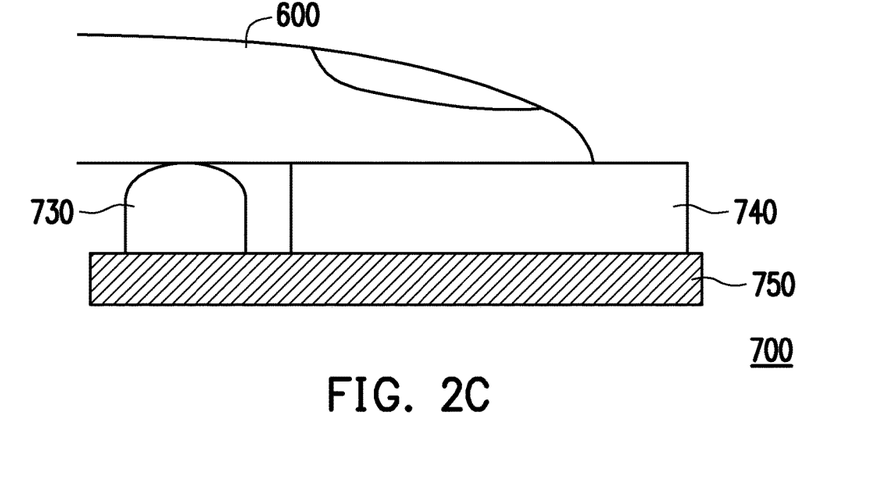
FIG. 2C is a schematic diagram of the fingerprint identification device according to yet another embodiment of the invention.

FIG. 2C is a schematic diagram of the fingerprint identification device according to yet another embodiment of the invention. Referring to FIG. 2C, in this embodiment, a fingerprint identification device 700 includes a light source 730, a light receiver 740, and a substrate 750. The light source 730 and the light receiver 740 are disposed on the substrate 750. In this embodiment, when an object 600 is directly placed on the light receiver 740, the light source 730 is driven to emit a light beam to the object 600. The light receiver 740 directly captures an object image from the object 600, so as to output a corresponding photocurrent signal to a processor of the fingerprint identification device.

In FIG. 2A to FIG. 2C as described above, the fingerprint identification devices 300, 500, and 700 of the exemplary embodiments respectively include a touch sensor. More specifically, in the fingerprint identification devices 300, 500, and 700 of the above exemplary embodiments, a conductive material, such as metal frame, is disposed in the pressing range of the object. The conductive material may cover a peripheral region of the pressing plate or a peripheral region of the light receiver, such that when a real finger touches the conductive material, the touch sensor generates the capacitance change by the signal provided by the conductive material, and then the touch sensor outputs the capacitive signal to the processors of the fingerprint identification devices 300, 500, and 700 according to the capacitance change. However, if a fake finger touches the conductive material, the touch sensor does not output the capacitive signal. Therefore, the fingerprint identification devices 300, 500, and 700 of the above exemplary embodiments are capable of preventing an inadvertent touch or identifying a fake finger.

However, in another embodiment, the fingerprint identification device 100 may further comprise an organic light emitting diode (OLED) display panel, and the organic light emitting diode display panel is disposed on a light receiving side of the light receiver 140. The organic light emitting diode display panel may be an active OLED display panel or a passive OLED display panel, wherein the active OLED display panel may include a plurality of pixel areas arranged in an array for planar display. In the another embodiment, the OLED display panel includes a light emitting layer, and the light emitting layer may be as the light source 130 and as described in the various embodiments of the present invention to provide a light beam to the object (user's finger). The light beam provided by the OLED display panel is a visible light beam. In the another embodiment, the light receiver 140 receives a portion of the light beam reflected by the object, so as to obtain an image of the object, and the light receiver 140 output an object image to the processor 110 of the fingerprint identification device 100. The processor 110 of fingerprint identification device 100 performs the fingerprint identification operation on the object image as described in the various embodiments of the present invention, so as to obtain the fingerprint identification result and the pixel change data.

Moreover, in yet another embodiment, the fingerprint identification device 100 may include another light source, wherein the another light source may configure to provide another light beam to the object, wherein the another light beam is a non-visible light beam. The another light source may be the infrared light source, but the invention is not limited thereto. In the another embodiment, the light receiver 140 may further receives a portion of the another light beam reflected by the object, so as to obtain another image of the object, and the light receiver 140 output another object image to the processor 110 of the fingerprint identification device 100. The processor 110 of fingerprint identification device 100 may further performs other fingerprint identification operations to obtain the fingerprint identification result, or performs other detection for other biological features. For example, the processor 110 determines whether the another object image of the object matches a registered fingerprint image as the fingerprint identification result, or obtains other biological features related to human. In addition, in yet another embodiment, the fingerprint identification device 100 may also be applied in the products for under-screen fingerprint recognition. The above OLED display panel may be a screen of a portable electronic device. That is to say, the above OLED display panel may provide fingerprint identification function and display function at the same time.

Figure 3:
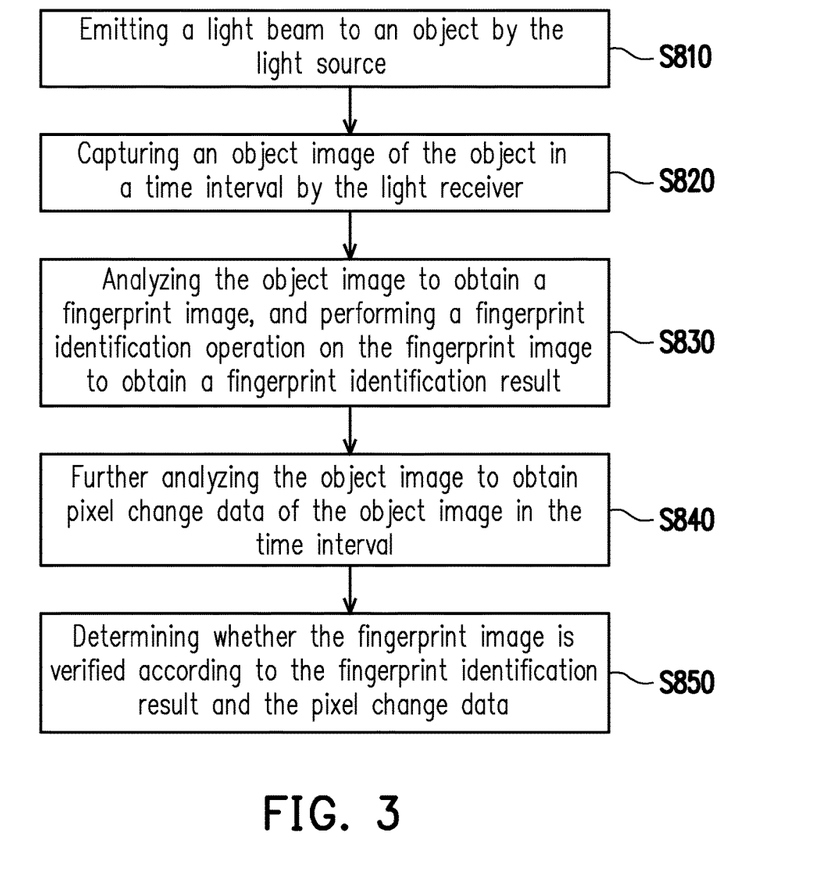
FIG. 3 is a flowchart of the fingerprint identification method according to an embodiment of the invention.

FIG. 3 is a flowchart of a fingerprint identification method according to an embodiment of the invention. Referring to FIG. 1 and FIG. 3, the fingerprint identification method of this embodiment is adapted for the fingerprint identification device of FIG. 1. In Step S810, the fingerprint identification device 100 emits a light beam to an object via the light source 130. In Step S820, the fingerprint identification device 100 captures an object image of the object in a time interval via the light receiver 140. In Step S830, the fingerprint identification device 100 analyzes the object image to obtain a fingerprint image and performs a fingerprint identification operation on the fingerprint image to obtain a fingerprint identification result via the processor 110.

In this embodiment, the light receiver 140 captures the object image of the object in a time interval, which is 10 seconds, for example. That is, the processor 110 may obtain an object image composed of a plurality of continuous object pictures. In this embodiment, the processor 110 may extract one of the continuous object pictures, e.g., the first object picture, for the fingerprint identification operation, but the invention is not limited thereto. In addition, the light receiver 140 of this embodiment may provide the object image in a YUV format, a RGB format, or a RAW RGB format to the processor 110, for example. In this embodiment, the processor 110 determines whether the fingerprint characteristic in the object image matches the registered fingerprint characteristic data that is stored in advance to determine a fingerprint identification result of the fingerprint image.

In Step S840, the processor 110 further analyzes the object image to obtain pixel change data of the object image in the time interval. In this embodiment, the processor 110 analyzes at least one partial block of each of the object pictures of the object image respectively to obtain a plurality of pieces of pixel data respectively corresponding to the object pictures in the time interval, and the processor 110 collects statistics of the pixel data to obtain the pixel change data.

Figure 4:
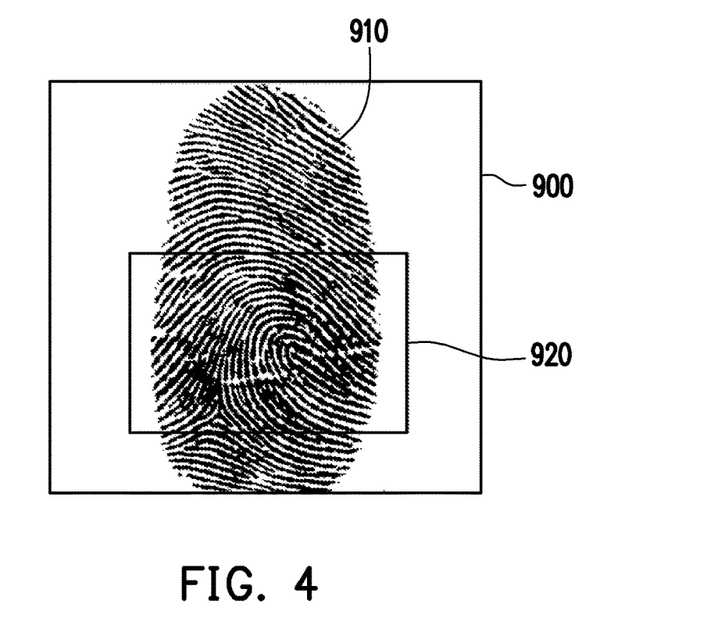
FIG. 4 is a view of the object picture according to an embodiment of the invention.
Figure 5:
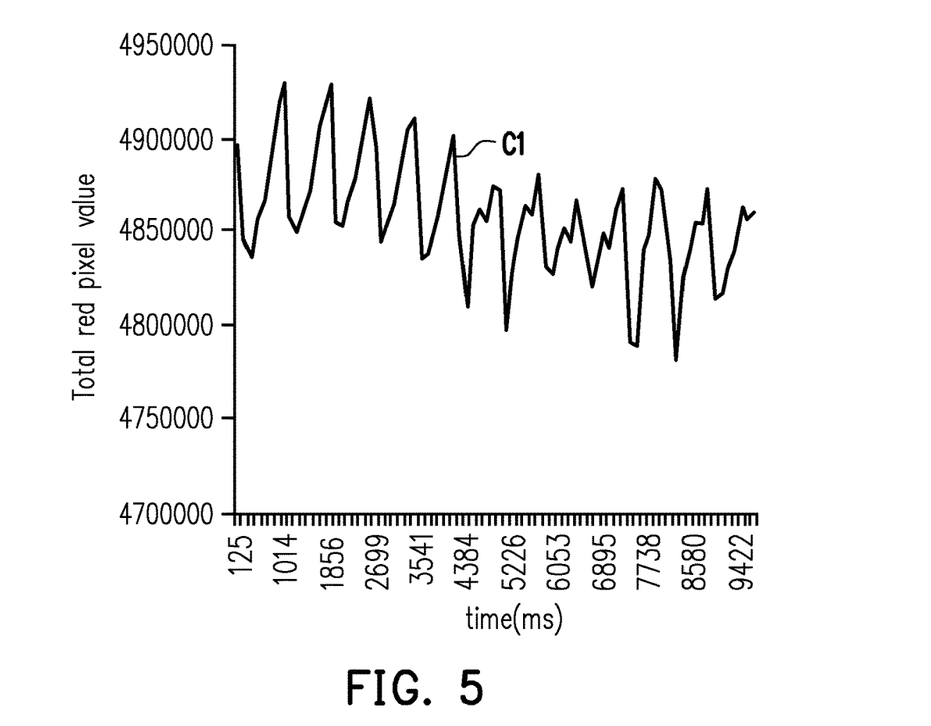
FIG. 5 is a schematic diagram of the pixel change data according to an embodiment of the invention.

For example, FIG. 4 is a view of the object picture according to an embodiment of the invention. FIG. 5 is a schematic diagram of the pixel change data according to an embodiment of the invention. Referring to FIG. 4, one object picture of the object image as described in each embodiment above may be an object picture 900 as shown in FIG. 4. In this example, the object picture 900 includes a fingerprint 910, and the number of pixels of the object picture 900 is 320×240, for example, but the invention is not limited thereto. In this example, the processor 110 may analyze a partial block picture 920 of the object picture 900, wherein the number of pixels of the block picture 920 is 220×108, for example. The processor 110 adds up the red pixel values of all the pixels of the block picture 920 to serve as pixel value information of the object picture 900. Alternatively, in an embodiment, the processor 110 adds up the total red pixel value, the total green pixel value, and the total blue pixel value of all the pixels of the block picture 920 to serve as the pixel value information of the object picture 900. In other words, the processor 110 may analyze each object picture of the object image to respectively obtain the respective pixel value information of the object pictures. Nevertheless, the block range and block size of the block picture 920 of the invention are not limited to the disclosure of FIG. 4 and may be decided according to different requirements.

Referring to FIG. 5, in this example, the processor 110 integrates the pixel value information of each object picture of the object image according to a corresponding time into the pixel change data as shown in FIG. 5. In FIG. 5, since there are capillaries under the surface of a real finger, if the object is a real finger, the total red pixel value of each object picture of the object image will change periodically with the heart rate. The processor 110 may collect statistics of the total red pixel value of each object picture in a time interval to obtain a curve C1. In this example, the processor 110 may determine whether the object is a real finger based on whether the curve C1 presents a periodical change in the time interval. The processor 110 may further generate heartbeat information according to a periodical change result of the curve C1 in the time interval. In other words, in addition to the function of fingerprint identification, the fingerprint identification device 100 further provides a function of detecting the heart rate of the user.

Therefore, in Step S850, the processor 110 determines whether the fingerprint image is verified according to the fingerprint identification result and the pixel change data described above. That is, if the processor 110 determines that the fingerprint identification result of the fingerprint image of the object matches the registered fingerprint characteristic data that is stored in advance, and the processor 110 determines that the pixel change data of the object image of the object presents a periodical change in the time interval of the sensing period, the processor 110 determines that the fingerprint image is verified. On the other hand, if the processor 110 determines that the fingerprint identification result of the fingerprint image of the object does not match the registered fingerprint characteristic data that is stored in advance, or the processor 110 determines that the pixel change data of the object image of the object does not present a periodical change in the time interval of the sensing period, the processor 110 determines that the fingerprint image fails to be verified.

To sum up, according to the fingerprint identification device and the fingerprint identification method of one or some embodiments of the invention, multiple object pictures are obtained by capturing an object image in a time interval. The fingerprint identification device of the invention may perform the fingerprint identification operation on one of the object pictures and analyze each of the object pictures to obtain the pixel change data of the object image of the object in the time interval. If the pixel change data of the object image presents a periodical change in the time interval, the fingerprint identification device determines that the object is a real finger. Therefore, in addition to performing the fingerprint identification operation, the fingerprint identification device of the invention may determine whether the object is a real finger, so as to prevent the fingerprint characteristic of a fake finger from being verified. Furthermore, the fingerprint identification device of the invention may also provide heartbeat information according to the pixel change data of the object image.

Although the invention has been described with reference to the embodiments thereof, it will be apparent to one of the ordinary skills in the art that modifications to the described embodiments may be made without departing from the spirit of the invention. Accordingly, the scope of the invention will be defined by the attached claims not by the above detailed description.

What is claimed is:

1. A fingerprint identification device, comprising:
   a light source, configured to emit a light beam to an object;
   a processor, coupled to the light source; and
   a light receiver, coupled to the processor, and configured to capture an object image of the object in a time interval,
   wherein the processor analyzes the object image, and extracts one of a plurality of object pictures of the object image to obtain a fingerprint image, and the processor performs a fingerprint identification operation on the fingerprint image to obtain a fingerprint identification result, wherein the processor further analyzes the object image to obtain pixel change data of the object image in the time interval, and the processor determines whether the fingerprint image is verified according to the fingerprint identification result and the pixel change data,
   wherein the processor analyzes a partial block of each of the object pictures respectively to obtain pixel data corresponding to the object pictures in the time interval, wherein the processor collects statistics of the pixel data to obtain the pixel change data,
   wherein the pixel data of each of the object pictures is a sum of a total red pixel value, the total green pixel value, and the total blue pixel value of all the pixels of the partial block of the block picture.

2. The fingerprint identification device according to claim 1, further comprising:
   a touch sensor, coupled to the processor, and configured to sense whether the object is placed on the touch sensor to output a sensing signal to the processor,
   wherein the processor determines whether to drive the light source to enable the light source to emit the light beam according to the sensing signal.

3. The fingerprint identification device according to claim 1, wherein the light beam emitted by the light source is a single-wavelength light beam or a multi-wavelength light beam.

4. The fingerprint identification device according to claim 1, wherein the processor analyzes the pixel change data to determine whether a pixel value in the pixel change data presents a periodical change in the time interval.

5. The fingerprint identification device according to claim 4, wherein when the processor determines that the pixel value in the pixel change data presents the periodical change in the time interval, the processor further generates heartbeat information according to a periodical change result of the pixel value in the time interval.

6. A fingerprint identification method, adapted for a fingerprint identification device, comprising:
   emitting a light beam to an object by a light source;
   capturing an object image of the object in a time interval by a light receiver,
   analyzing the object image and extracting one of a plurality of object pictures of the object image to obtain a fingerprint image, and performing a fingerprint identification operation on the fingerprint image to obtain a fingerprint identification result;
   further analyzing the object image to obtain pixel change data of the object image in the time interval, wherein further analyzing the object image to obtain the pixel change data of the object image in the time interval comprises:
      analyzing a partial block of each of the object pictures respectively to obtain pixel data corresponding to the object pictures in the time interval; and
      collecting statistics of the pixel data to obtain the pixel change data,
      wherein the pixel data of each of the object pictures is a sum of a total red pixel value, the total green pixel value, and the total blue pixel value of all the pixels of the partial block of the block picture; and
   determining whether the fingerprint image is verified according to the fingerprint identification result and the pixel change data.

7. The fingerprint identification method according to claim 6, further comprising:
   sensing whether the object is placed on a touch sensor to output a sensing signal by the touch sensor; and determining whether to drive the light source to enable the light source to emit the light beam according to the sensing signal.

8. The fingerprint identification method according to claim 6, wherein the light beam emitted by the light source is a single-wavelength light beam or a multi-wavelength light beam.

9. The fingerprint identification method according to claim 6, wherein determining whether the fingerprint image is verified according to the fingerprint identification result and the pixel change data comprises:
analyzing the pixel change data to determine whether a pixel value in the pixel change data presents a periodical change in the time interval.

10. The fingerprint identification method according to claim 9, further comprising:
further generating heartbeat information according to a periodical change result of the pixel value in the time interval when the pixel value in the pixel change data presents the periodical change in the time interval.

11. A fingerprint identification device, comprising:
an organic light emitting diode display panel, comprises a light source configured to emit a light beam to an object;
a processor, coupled to the light source and the organic light emitting diode display panel; and
a light receiver, coupled to the processor, and configured to capture an object image of the object in a time interval,
wherein the processor analyzes the object image, and extracts one of a plurality of object pictures of the object image to obtain a fingerprint image, and the processor performs a fingerprint identification operation on the fingerprint image to obtain a fingerprint identification result, wherein the processor further analyzes the object image to obtain pixel change data of the object image in the time interval, and the processor determines whether the fingerprint image is verified according to the fingerprint identification result and the pixel change data,
wherein the processor analyzes a partial block of each of the object pictures respectively to obtain pixel data corresponding to the object pictures in the time interval, wherein the processor collects statistics of the pixel data to obtain the pixel change data,
wherein the pixel data of each of the object pictures is a sum of a total red pixel value, the total green pixel value, and the total blue pixel value of all the pixels of the partial block of the block picture,
wherein the processor analyzes the pixel change data to determine whether a pixel value in the pixel change data presents a periodical change in the time interval,
wherein when the processor determines that the pixel value in the pixel change data presents the periodical change in the time interval, the processor further generates heartbeat information according to a periodical change result of the pixel value in the time interval.

12. A fingerprint identification method, adapted for a fingerprint identification device, comprising:
emitting a light beam to an object by a light source of an organic light emitting diode display panel;
capturing an object image of the object in a time interval by a light receiver;
analyzing the object image and extracting one of a plurality of object pictures of the object image to obtain a fingerprint image, and performing a fingerprint identification operation on the fingerprint image to obtain a fingerprint identification result;
further analyzing the object image to obtain pixel change data of the object image in the time interval, wherein further analyzing the object image to obtain the pixel change data of the object image in the time interval comprises:
analyzing a partial block of each of the object pictures respectively to obtain pixel data corresponding to the object pictures in the time interval; and
collecting statistics of the pixel data to obtain the pixel change data,
wherein the pixel data of each of the object pictures is a sum of a total red pixel value, the total green pixel value, and the total blue pixel value of all the pixels of the partial block of the block picture;
determining whether the fingerprint image is verified according to the fingerprint identification result and the pixel change data, wherein determining whether the fingerprint image is verified according to the fingerprint identification result and the pixel change data comprises:
analyzing the pixel change data to determine whether a pixel value in the pixel change data presents a periodical change in the time interval; and
further generating heartbeat information according to a periodical change result of the pixel value in the time interval when the pixel value in the pixel change data presents the periodical change in the time interval.

\* \* \* \* \*